(12) United States Patent
Lin et al.

(10) Patent No.: US 12,258,636 B2
(45) Date of Patent: Mar. 25, 2025

(54) METHODS FOR EARLY PREDICTION, TREATMENT RESPONSE, RECURRENCE AND PROGNOSIS MONITORING OF PANCREATIC CANCER

(71) Applicants: EG BIOMED CO., LTD., Taipei (TW); EG BIOMED AU PTY LTD, Melbourne (AU)

(72) Inventors: Ruo-Kai Lin, Taipei (TW); Hsieh-Tsung Shen, Taipei (TW)

(73) Assignees: EG BIOMED CO., LTD., Taipei (TW); EG BIOMED AU PTY LTD, Melbourne (AU)

( * ) Notice: Subject to any disclaimer, the term of this patent is extended or adjusted under 35 U.S.C. 154(b) by 0 days.

(21) Appl. No.: 18/444,053

(22) Filed: Feb. 16, 2024

(65) Prior Publication Data
US 2024/0279744 A1    Aug. 22, 2024

Related U.S. Application Data

(60) Provisional application No. 63/485,748, filed on Feb. 17, 2023.

(51) Int. Cl.
*C12Q 1/6886* (2018.01)
(52) U.S. Cl.
CPC ..... *C12Q 1/6886* (2013.01); *C12Q 2600/154* (2013.01)
(58) Field of Classification Search
None
See application file for complete search history.

(56) References Cited

U.S. PATENT DOCUMENTS

| 5,541,308 A * | 7/1996 | Hogan ............... C12Q 1/689 435/6.12 |
| 11,821,039 B2 | 11/2023 | Ahlquist et al. |
| 2016/0040246 A1 * | 2/2016 | Ahlquist ............ C12Q 1/6886 506/2 |
| 2019/0330703 A1 | 10/2019 | Widschwendter et al. |
| 2020/0283853 A1 | 9/2020 | Ahlquist et al. |

FOREIGN PATENT DOCUMENTS

| WO | 2014159652 A2 | 10/2014 |
| WO | 2021253138 A1 | 12/2021 |
| WO | 2022157764 A1 | 7/2022 |

OTHER PUBLICATIONS

Diffenbach (PCR methods and Applications (1993) vol. 3, pp. S30-S37) (Year: 1993).*
Roux et al(PCR Methods and Applications (1995) vol. 4, pp. s185-s194) (Year: 1995).*
International Search Report and Written Opinion issued on May 28, 2024 in International Patent Application No. PCT/AU2024/50116.
Mishra, Nitish Kumar and Guda, Chittibabu, "Genome-wide DNA methylation analysis reveals molecular subtypes of pancreatic cancer," Oncotarget, 2017, vol. 8, No. 17, pp. 28990-29012.

* cited by examiner

*Primary Examiner* — Katherine D Salmon
(74) *Attorney, Agent, or Firm* — Prosyla Group PC

(57) ABSTRACT

The present invention discloses a set of novel epigenetic biomarkers for early prediction, treatment response, recurrence and prognosis monitoring of pancreatic cancer. Aberrant methylation of genes can be detected in tumor tissues and plasma samples from pancreatic cancer patients but not in normal healthy individual. The present disclosure also discloses primers and probes used herein.

23 Claims, 7 Drawing Sheets

Specification includes a Sequence Listing.

METHODS FOR EARLY PREDICTION, TREATMENT RESPONSE, RECURRENCE AND PROGNOSIS MONITORING OF PANCREATIC CANCER

PRIORITY INFORMATION

This application claims benefit of and priority to U.S. Provisional Patent Application No. 63/485,748, filed Feb. 17, 2023, the contents of which is incorporated by reference in its entirety.

SEQUENCE LISTING

The instant application contains a Sequence Listing which is submitted electronically in .xml format and is hereby incorporated by reference in its entirety. The .xml copy, created on Feb. 16, 2024, is named "G4590-17700US_20240216_SeqListing.xml" and is 12 kilobytes in size.

FIELD OF THE INVENTION

The present disclosure relates to gene biomarkers for prediction of risk or susceptibility of pancreatic cancer and/or prognosis and malignancy of pancreatic cancer. Particularly, the present disclosure assesses methylation of the gene biomarkers to detect a pancreatic cancer and predicts risk of a pancreatic cancer or susceptibility to a pancreatic cancer and/or prognosis and malignancy of the pancreatic cancer.

BACKGROUND OF THE INVENTION

Cancer is a group of diseases involving abnormal cell growth with the potential to invade or spread to other parts of the body and is a leading cause of deaths worldwide.

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression.

US 20080311570A1 provides a method for screening cancer that comprises the following steps: (1) providing a test specimen; (2) detecting the methylation status of the CpG sequence in at least one target gene within the genomic DNA of the test specimen, wherein the target genes consist of SOX1, PAX1, LMX1A, NKX6-1, WT1 and ONECUT1; and (3) determining whether there is cancer or cancerous pathological change in the specimen based on the presence or absence of the methylation status in the target gene. WO 2016071477A1 relates to assessing the response of a cancer patient to a treatment by analyzing CpG methylation in the shox2 gene. EP2828405B1 provides methods for detecting colorectal neoplasia by evaluating multiple gene markers in blood or plasma and stool.

However, the current techniques in detection of pancreatic cancer are not satisfactory.

SUMMARY OF THE INVENTION

The present disclosure relates to one or more novel epigenetic biomarkers for early prediction, treatment response, recurrence and prognosis monitoring of pancreatic cancer. Aberrant methylation of genes can be detected in tumor tissues and plasma samples from cancer patients but not in normal healthy individuals. The present disclosure also discloses primers and probes used herein.

Detection of Pancreatic Cancer

In one embodiment, the present disclosure provides a method for detecting the methylation status in a subject who is in a need of detection of pancreatic cancer or detecting a predisposition to, or the incidence of, pancreatic cancer or predicting treatment response, prognosis or recurrence of pancreatic cancer in the subject, wherein the method comprises:

(a) providing a biological sample containing DNA from the subject, wherein the DNA comprises a target gene ZFP30 or a fragment thereof;

(b) assaying methylation status of one or more epigenetic biomarkers with CpG site in the target gene ZFP30 or the fragment thereof; and (c) identifying the target gene ZFP30 or the fragment thereof in the biological sample having higher methylation level relative to that of healthy individuals as hypermethylation, wherein the hypermethylation of the target gene ZFP30 or the fragment thereof is indicative of pancreatic cancer or predisposition to, or the incidence, poor treatment response, poor prognosis or recurrence of, the pancreatic cancer.

In some embodiments, the methylation status is detected by polymerase chain reaction (PCR), nucleic acid sequencing (such as bisulfite sequencing or pyrosequencing), bisulfite conversion, mass spectrometry, methylation specific nuclease, mass-based separation, target capture, microarray, or a combination thereof. In a particular embodiment, the methylation status is detected by PCR, such as methylation specific PCR (MSP), real-time methylation specific PCR, quantitative methylation-specific PCR (QMSP), methylation sensitive DNA restriction enzyme analysis, bisulfite genomic sequencing PCR, or PCR using a methylated DNA-specific binding protein.

In some embodiments, the assaying methylation status in (b) comprises extracting genomic DNA from a biological sample of a subject suspected of having or having a pancreatic cancer; amplifying the genomic DNA with primers consisting of a pair of primers specific for ZFP30 and measuring the methylation level of one or more CpG sites in ZFP30 by a polymerase chain reaction (PCR). In a further embodiment, assaying methylation status in (b) further comprises treating the resulting extract with bisulfate after extracting genomic DNA from a biological sample; and bisulfite-treated genomic DNA is amplified.

In some embodiments, the assaying methylation status in (b) comprises assaying methylation status of two, three, four, five, six, seven or more epigenetic biomarkers with CpG site in the target gene ZFP30 or the fragment thereof.

Certain embodiments of a pair of primers specific for ZFP30 used to amplify the genomic DNA or bisulfite-treated genomic DNA have sequence identity of about 85%, about 86%, about 87%, about 88%, about 89%, about 90%, about 91%, about 92%, about 93%, about 94%, about 95%, about 96%, about 97%, about 98%, about 99%, or about 100% to sequences of SEQ ID NOs: 1 and 2.

In some embodiments, a ZFP30 methylation specific probe is used to assay the methylation level of the target gene ZFP30 or the fragment thereof. In some embodiments, the ZFP30 methylation specific probe has a sequence with at least 85% identity to SEQ ID No: 9. In some embodiments, the ZFP30 methylation specific probe has a sequence with about 85%, about 86%, about 87%, about 88%, about 89%, about 90%, about 91%, about 92%, about 93%, about 94%, about 95%, about 96%, about 97%, about 98%, about 99%, or about 100% identity to SEQ ID No: 9. In one embodiment, the ZFP30 methylation specific probe has the sequence of SEQ ID No: 9.

In one embodiment, the one, two or more epigenetic biomarkers with CpG site locate in Chr19 37692300-37692450 of the target gene ZFP30.

In one embodiment, the present disclosure provides a method for detecting the methylation status in a subject who is in a need of detection of pancreatic cancer or detecting a predisposition to, or the incidence of, pancreatic cancer or predicting treatment response, prognosis or recurrence of pancreatic cancer in the subject, wherein the method comprises:
  (ai) providing a biological sample containing DNA from the subject, wherein the DNA comprises a target gene FBXL7 or a fragment thereof;
  (bi) assaying methylation status of one or more epigenetic biomarkers with CpG site in the target gene FBXL7 or the fragment thereof; and
  (ci) identifying the target gene FBXL7 or the fragment thereof in the biological sample having higher methylation level relative to that of healthy individuals as hypermethylation, wherein the hypermethylation of the target gene FBXL7 or the fragment thereof is indicative of pancreatic cancer or predisposition to, or the incidence, poor treatment response, poor prognosis or recurrence of, the pancreatic cancer.

In some embodiments, the methylation status is detected by polymerase chain reaction (PCR), nucleic acid sequencing (such as bisulfite sequencing or pyrosequencing), bisulfite conversion, mass spectrometry, methylation specific nuclease, mass-based separation, target capture, microarray, or a combination thereof. In a particular embodiment, the methylation status is detected by PCR, such as methylation specific PCR (MSP), real-time methylation specific PCR, quantitative methylation-specific PCR (QMSP), methylation sensitive DNA restriction enzyme analysis, bisulfite genomic sequencing PCR, or PCR using a methylated DNA-specific binding protein.

In some embodiments, the assaying methylation status in (bi) comprises extracting genomic DNA from a biological sample of a subject suspected of having or having a pancreatic cancer; amplifying the genomic DNA with primers consisting of a pair of primers specific for FBXL7 and measuring the methylation level of one or more CpG sites in FBXL7 by a polymerase chain reaction (PCR). In a further embodiment, assaying methylation status in (bi) further comprises treating the resulting extract with bisulfate after extracting genomic DNA from a biological sample; and bisulfite-treated genomic DNA is amplified.

In some embodiments, the assaying methylation status in (bi) comprises assaying methylation status of two, three, four, five, six, seven or more epigenetic biomarkers with CpG site in the target gene FBXL7 or the fragment thereof.

Certain embodiments of a pair of primers specific for FBXL7 used to amplify the genomic DNA or bisulfite-treated genomic DNA have sequence identity of about 85%, about 86%, about 87%, about 88%, about 89%, about 90%, about 91%, about 92%, about 93%, about 94%, about 95%, about 96%, about 97%, about 98%, about 99%, or about 100% to sequences of SEQ ID NOs: 3 and 4.

In some embodiments, a FBXL7 methylation specific probe is used to assay the methylation level of the target gene FBXL7 or the fragment thereof. In some embodiments, the FBXL7 methylation specific probe has a sequence with at least 85% identity to SEQ ID No: 10. In some embodiments, the FBXL7 methylation specific probe has a sequence with about 85%, about 86%, about 87%, about 88%, about 89%, about 90%, about 91%, about 92%, about 93%, about 94%, about 95%, about 96%, about 97%, about 98%, about 99%, or about 100% identity to SEQ ID No: 10. In one embodiment, the FBXL7 methylation specific probe has the sequence of SEQ ID No: 10.

In one embodiment, the one, two, three or more epigenetic biomarkers with CpG site locate in Chr5 15500544-15500694 of the target gene FBXL7.

In a further embodiment, the present disclosure provides a method for detecting the methylation status in a subject who is in a need of detection of pancreatic cancer or detecting a predisposition to, or the incidence of, pancreatic cancer or predicting treatment response, prognosis or recurrence of pancreatic cancer in the subject, wherein the method comprises:
  (aii) providing a biological sample containing DNA from the subject, wherein the DNA comprises a target gene ZFP30 or a fragment thereof and a target gene FBXL7 or a fragment thereof;
  (bii) assaying methylation status of one or more epigenetic biomarkers with CpG site in the target gene ZFP30 or the fragment thereof and methylation status of one or more epigenetic biomarkers with CpG site in the target gene FBXL7 or the fragment thereof; and
  (cii) identifying the target genes ZFP30 and FBXL7 or the fragment thereof in the biological sample having higher methylation level relative to that of healthy individuals as hypermethylation, wherein the hypermethylation of the target genes ZFP30 and FBXL7 or the fragment thereof is indicative of pancreatic cancer or predisposition to, or the incidence, poor treatment response, poor prognosis or recurrence of, the pancreatic cancer.

In some embodiments, the methylation status is detected by polymerase chain reaction (PCR), nucleic acid sequencing (such as bisulfite sequencing or pyrosequencing), bisulfite conversion, mass spectrometry, methylation specific nuclease, mass-based separation, target capture, microarray, or a combination thereof. In a particular embodiment, the methylation status is detected by PCR, such as methylation specific PCR (MSP), real-time methylation specific PCR, quantitative methylation-specific PCR (QMSP), methylation sensitive DNA restriction enzyme analysis, bisulfite genomic sequencing PCR, or PCR using a methylated DNA-specific binding protein.

In some embodiments, the assaying methylation status in (bii) comprises extracting genomic DNA from a biological sample of a subject suspected of having or having a pancreatic cancer; amplifying the genomic DNA with primers consisting of a pair of primers specific for ZFP30 and a primer pair specific for FBXL7 and measuring the methylation level of one or more CpG sites in ZFP30 and the methylation level of one or more CpG sites in FBXL7 by a polymerase chain reaction (PCR). In a further embodiment, assaying methylation status in (bii) further comprises treating the resulting extract with bisulfate after extracting genomic DNA from a biological sample; and bisulfite-treated genomic DNA is amplified.

Certain embodiments of a pair of primers specific for ZFP30 used to amplify the genomic DNA or bisulfite-treated genomic DNA have sequence identity of about 85%, about 86%, about 87%, about 88%, about 89%, about 90%, about 91%, about 92%, about 93%, about 94%, about 95%, about 96%, about 97%, about 98%, about 99%, or about 100% to sequences of SEQ ID NOs: 1 and 2. Certain embodiments of a pair of primers specific for FBXL7 used to amplify the genomic DNA or bisulfite-treated genomic DNA have sequence identity of about 85%, about 86%, about 87%, about 88%, about 89%, about 90%, about 91%, about 92%, about 93%, about 94%, about 95%, about 96%, about 97%, about 98%, about 99%, or about 100% to sequences of SEQ ID NOs: 3 and 4.

In some embodiments, a ZFP30 methylation specific probe and a FBXL7 methylation specific probe are used to assay the methylation level of the target gene ZFP30 or the fragment thereof and the target gene FBXL7 or the fragment thereof. In some embodiments, the ZFP30 methylation specific probe has a sequence with at least 85% identity to SEQ ID No: 9. In some embodiments, the ZFP30 methylation specific probe has a sequence with about 85%, about 86%, about 87%, about 88%, about 89%, about 90%, about 91%, about 92%, about 93%, about 94%, about 95%, about 96%, about 97%, about 98%, about 99%, or about 100% identity to SEQ ID No: 9. In one embodiment, the ZFP30 methylation specific probe has the sequence of SEQ ID No: 9. In some embodiments, the FBXL7 methylation specific probe has a sequence with at least 85% identity to SEQ ID No: 10. In some embodiments, the FBXL7 methylation specific probe has a sequence with about 85%, about 86%, about 87%, about 88%, about 89%, about 90%, about 91%, about 92%, about 93%, about 94%, about 95%, about 96%, about 97%, about 98%, about 99%, or about 100% identity to SEQ ID No: 10. In one embodiment, the FBXL7 methylation specific probe has the sequence of SEQ ID No: 10.

In some embodiments, the assaying methylation status in (bii) comprises assaying methylation status of two or more epigenetic biomarkers with CpG site in the target gene ZFP30 or the fragment thereof and methylation status of two, three or more epigenetic biomarkers with CpG site in the target gene FBXL7 or the fragment thereof In one embodiment, the one, two or more epigenetic biomarkers with CpG site locate in Chr19 37692300-37692450 of the target gene ZFP30.

In one embodiment, the one, two, three or more epigenetic biomarkers with CpG site locate in Chr5 15500544-15500694 of the target gene FBXL7.

In some embodiments, in (a), (ai) or (aii) of the method, the DNA further comprises one or more of target genes CNTN4 and KLRG2 or fragments thereof;
  (biii) further comprises assaying methylation status of epigenetic biomarkers in one or more of the target genes CNTN4 and KLRG2 or the fragments thereof; and
  (ciii) further comprises identifying one or more of the target genes CNTN4 and KLRG2 or fragments thereof in the biological sample having higher methylation level relative to that of a control gene compared to healthy individuals as hypermethylation, wherein the hypermethylation of the target genes ZFP30, FBXL7 and one or more of CNTN4 and KLRG2 is indicative of pancreatic cancer or predisposition to, or the incidence, poor treatment response, poor prognosis or recurrence of, the pancreatic cancer.

In some embodiments, the methylation status is detected by polymerase chain reaction (PCR), nucleic acid sequencing (such as bisulfite sequencing or pyrosequencing), bisulfite conversion, mass spectrometry, methylation specific nuclease, mass-based separation, target capture, microarray, or a combination thereof. In a particular embodiment, the methylation status is detected by PCR, such as methylation specific PCR (MSP), real-time methylation specific PCR, quantitative methylation-specific PCR (QMSP), methylation sensitive DNA restriction enzyme analysis, bisulfite genomic sequencing PCR, or PCR using a methylated DNA-specific binding protein.

In some embodiments, the assaying methylation status in (biii) comprises extracting genomic DNA from a biological sample of a subject suspected of having or having a pancreatic cancer; amplifying the genomic DNA with primers consisting of a pair of primers specific for CNTN4 and/or a primer pair specific for KLRG2 and measuring the methylation level of one or more CpG sites in CNTN4 and/or the methylation level of one or more CpG sites in KLRG2 by a polymerase chain reaction (PCR). In a further embodiment, assaying methylation status in (biii) further comprises treating the resulting extract with bisulfate after extracting genomic DNA from a biological sample; and bisulfite-treated genomic DNA is amplified.

Certain embodiments of a pair of primers specific for CNTN4 used to amplify the genomic DNA or bisulfite-treated genomic DNA have sequence identity of about 85%, about 86%, about 87%, about 88%, about 89%, about 90%, about 91%, about 92%, about 93%, about 94%, about 95%, about 96%, about 97%, about 98%, about 99%, or about 100% to sequences of SEQ ID NOs: 5 and 6.

Certain embodiments of a pair of primers specific for KLRG2 used to amplify the genomic DNA or bisulfite-treated genomic DNA have sequence identity of about 85%, about 86%, about 87%, about 88%, about 89%, about 90%, about 91%, about 92%, about 93%, about 94%, about 95%, about 96%, about 97%, about 98%, about 99%, or about 100% to sequences of SEQ ID NOs: 7 and 8.

In some embodiments, a CNTN4 methylation specific probe, a KLRG2 methylation specific probe, or a combination thereof is used to assay the methylation level of one or more of the target genes CNTN4 and KLRG2 DNA or the fragments thereof and a control DNA sequence in the biological sample.

In some embodiments, the CNTN4 methylation specific probe has a sequence with at least 85% identity to SEQ ID No: 11. In some embodiments, the CNTN4 methylation specific probe has a sequence with about 85%, about 86%, about 87%, about 88%, about 89%, about 90%, about 91%, about 92%, about 93%, about 94%, about 95%, about 96%, about 97%, about 98%, about 99%, or about 100% identity to SEQ ID No: 11. In one embodiment, the CNTN4 methylation specific probe has the sequence of SEQ ID No: 11.

In some embodiments, the KLRG2 methylation specific probe has a sequence with at least 85% identity to SEQ ID No: 12. In some embodiments, the KLRG2 methylation specific probe has a sequence with about 85%, about 86%, about 87%, about 88%, about 89%, about 90%, about 91%, about 92%, about 93%, about 94%, about 95%, about 96%, about 97%, about 98%, about 99%, or about 100% identity to SEQ ID No: 12. In one embodiment, the KLRG2 methylation specific probe has the sequence of SEQ ID No: 12.

In some embodiments, the biological sample described herein is a tissue sample, a pancreatic juice sample, a pancreatic cyst fluid sample, a stool sample, cell sample, blood sample, urine sample, serum sample or plasma sample.

In some embodiments, the present disclosure further provides a kit for detecting the methylation status in a subject who is in a need of detection of pancreatic cancer or detecting a predisposition to, or the incidence of, pancreatic cancer or predicting treatment response, prognosis or recurrence of pancreatic cancer in a subject, which comprises a primer pair having the sequences of SEQ ID NOs: 1 and 2 and/or a probe having the sequence of SEQ ID No: 9 for assaying methylation status of epigenetic biomarkers in target gene ZFP30 or fragments thereof.

In some embodiments, the kit further comprises a primer pair having the sequences of SEQ ID NOs: 3 and 4 and/or a probe having the sequence of SEQ ID No: 10 for assaying methylation status of epigenetic biomarkers in target gene FBXL7 or fragments thereof.

In some embodiments, the kit further comprises a primer pair having the sequences of SEQ ID NOs: 5 and 6 and/or a probe having the sequence of SEQ ID No: 11 for assaying methylation status of epigenetic biomarkers in target gene CNTN4 or fragments thereof and/or a primer pair having the sequences of SEQ ID NOs: 7 and 8 and/or a probe having the sequence of SEQ ID No: 12 for assaying methylation status of epigenetic biomarkers in target gene KLRG2 or fragments thereof.

In some embodiments, the kit further comprises sodium bisulfite and adapters for whole target genes amplification, and polynucleotides (e.g., detectably-labeled polynucleotides) to quantify the presence of the converted methylated and or the converted unmethylated sequence of at least one cytosine from a DNA region of epigenetic biomarkers in target genes. In some embodiments, the kit further comprises methylation sensing restriction enzymes for whole target sequence or genes amplification.

In one embodiment, the present disclosure provides a method for measuring the methylation level of one or more CpG sites in ZFP30 or a fragment thereof comprising:
  extracting genomic DNA from a biological sample of a subject suspected of having or having a pancreatic cancer;
  treating the resulting extract with bisulfate;
  amplifying the bisulfite-treated genomic DNA with primers consisting of a pair of primers specific for ZFP30; and
  measuring the methylation level of one or more CpG sites in ZFP30 by a polymerase chain reaction (PCR).

In some further embodiments, the method further comprises measuring the methylation level of one or more CpG sites in CNTN4 and/or KLRG2 or a fragment thereof comprising: extracting genomic DNA from a biological sample of a subject suspected of having or having a pancreatic cancer; treating the resulting extract with bisulfate; amplifying the bisulfite-treated genomic DNA with primers consisting of a pair of primers specific for CNTN4 or a fragment thereof and/or primers consisting of a pair of primers specific for KLRG2 or a fragment thereof; and measuring the methylation level of one or more CpG sites in CNTN4 and/or KLRG2 or a fragment thereof by a polymerase chain reaction (PCR).

In one embodiment, the present disclosure provides a method for measuring the methylation level of one or more (such as two, three, four, five, six, seven or more) CpG sites in FBXL7 or a fragment thereof comprising: extracting genomic DNA from a biological sample of a subject suspected of having or having a pancreatic cancer; treating the resulting extract with bisulfate; amplifying the bisulfite-treated genomic DNA with primers consisting of a pair of primers specific for FBXL7; and measuring the methylation level of one or more CpG sites in FBXL7 by a polymerase chain reaction (PCR).

In some further embodiments, the method further comprises measuring the methylation level of one or more ((such as two, three, four, five, six, seven or more)) CpG sites in CNTN4 and/or KLRG2 or a fragment thereof comprising: extracting genomic DNA from a biological sample of a subject suspected of having or having a pancreatic cancer; treating the resulting extract with bisulfate; amplifying the bisulfite-treated genomic DNA with primers consisting of a pair of primers specific for CNTN4 or a fragment thereof and/or primers consisting of a pair of primers specific for KLRG2 or a fragment thereof; and measuring the methylation level of one or more CpG sites (such as two, three, four, five, six, seven or more) in CNTN4 and/or KLRG2 or a fragment thereof by a polymerase chain reaction (PCR).

In one embodiment, the present disclosure provides a method for measuring the methylation level of one or more CpG sites in ZFP30 or a fragment thereof and FBXL7 or a fragment thereof comprising: extracting genomic DNA from a biological sample of a subject suspected of having or having a pancreatic cancer; treating the resulting extract with bisulfite; amplifying the bisulfite-treated genomic DNA with primers consisting of a pair of primers specific for ZFP30 and a primer pair specific for FBXL7, and measuring the methylation level of one or more CpG sites in ZFP30 and FBXL7 by a polymerase chain reaction (PCR).

In some further embodiments, the method further comprises measuring the methylation level of one or more CpG sites in CNTN4 and/or KLRG2 or a fragment thereof comprising: extracting genomic DNA from a biological sample of a subject suspected of having or having a pancreatic cancer; treating the resulting extract with bisulfate; amplifying the bisulfite-treated genomic DNA with primers consisting of a pair of primers specific for CNTN4 or a fragment thereof and/or primers consisting of a pair of primers specific for KLRG2 or a fragment thereof; and measuring the methylation level of one or more CpG sites in CNTN4 and/or KLRG2 or a fragment thereof by a polymerase chain reaction (PCR).

In some embodiments, the PCR described herein is methylation-specific PCR, quantitative methylation-specific PCR, methylation sensitive DNA restriction enzyme analysis or bisulfite genomic sequencing PCR.

In one embodiment, the present disclosure provides a method comprising: extracting genomic DNA from a biological sample obtained from a subject; treating the extracted genomic DNA with bisulfite; and amplifying the bisulfite-treated genomic DNA using primers specific for a CpG site for ZFP30, primers specific for a CpG site for FBXL7, or primers specific for a CpG site for ZFP30 and primers specific for a CpG site for FBXL7; and measuring a methylation level of the CpG site for ZFP30, or a methylation level of the CpG site for FBXL7, or a methylation level of the CpG site for ZFP30 and the CpG site for FBXL7.

In some further embodiments, the method further comprises extracting genomic DNA from a biological sample obtained from a subject; treating the extracted genomic DNA with bisulfite; and amplifying the bisulfite-treated genomic DNA using primers specific for a CpG site for CNTN4, primers specific for a CpG site for KLRG2, or primers specific for a CpG site for CNTN4 and primers specific for a CpG site for KLRG2; and measuring a methylation level of the CpG site for CNTN4, or a methylation level of the CpG site for KLRG2, or a methylation level of the CpG site for CNTN4 and the CpG site for KLRG2.

Certain embodiments of primers described herein have sequence identity of about 85%, about 86%, about 87%, about 88%, about 89%, about 90%, about 91%, about 92%, about 93%, about 94%, about 95%, about 96%, about 97%, about 98%, about 99%, or about 100% to a sequence(s) selected from the group consisting of SEQ ID Nos: 1 to 8. In some embodiments, primers having sequences of SEQ ID Nos: 1 to 8. In some embodiments, probes having sequences of SEQ ID Nos: 9 to 12 are used to detect or measure the methylation status of one or more of the target genes ZFP30, FBXL7, CNTN4, and KLRG2 or fragments thereof.

In a further embodiment, the measuring a methylation level of the CpG site is determined by PCR. In some embodiments, the PCR described herein is methylation-specific PCR, quantitative methylation-specific PCR, methylation sensitive DNA restriction enzyme analysis or bisulfite genomic sequencing PCR.

BRIEF DESCRIPTION OF THE DRAWINGS

FIG. 1B: FBXL7; FIG. 1C: CNTN4; and FIG. 1D: KLRG2). The darker bands represent the methylation sites on the genes.

DETAILED DESCRIPTION OF THE INVENTION

Figure 1A:
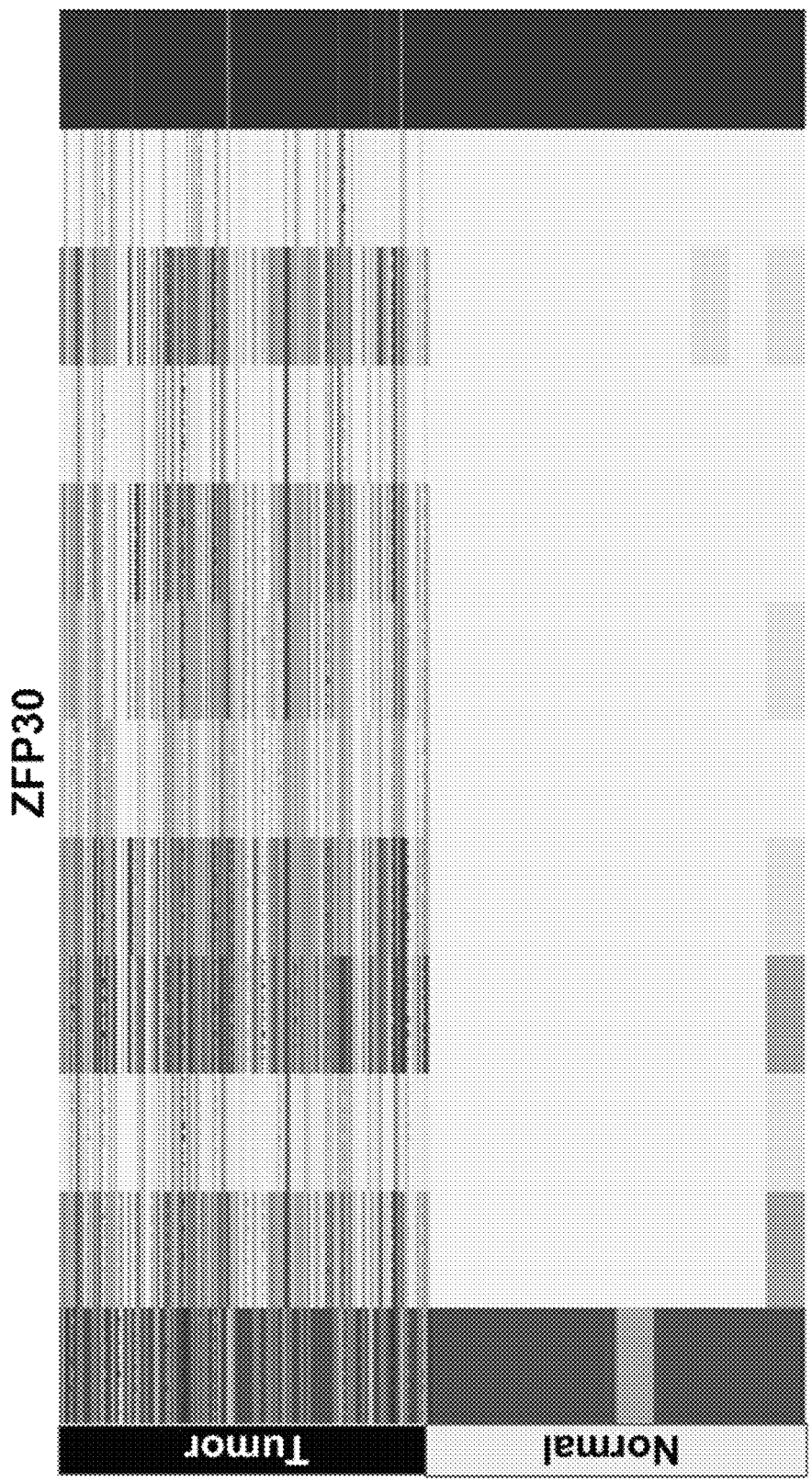
FIGS. 1A-1D show the heatmaps for difference of methylation status of several target genes between tumor tissues and adjacent normal tissues (FIG. 1A: ZFP30.
Figure 1B:
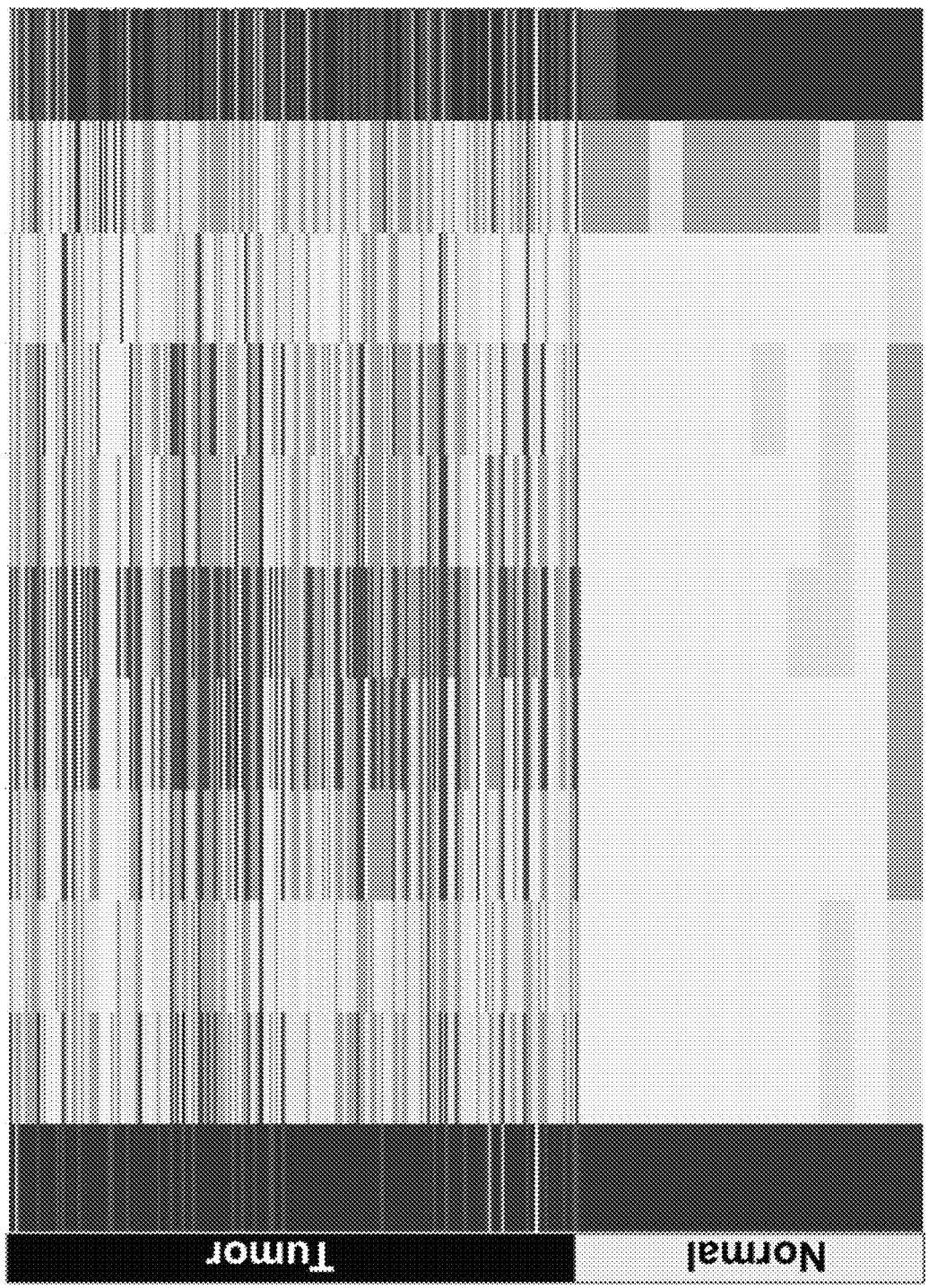
Figure 1C:
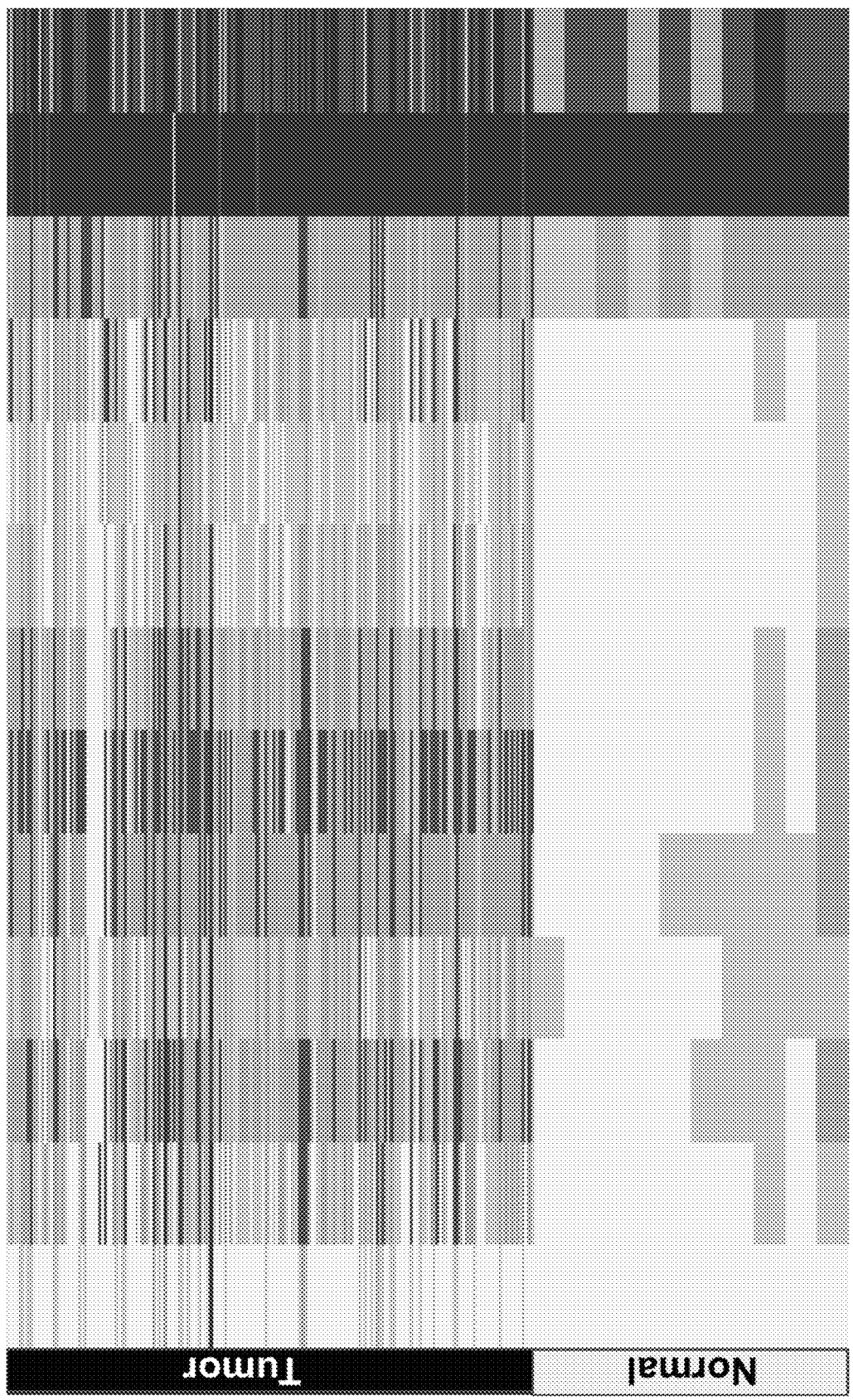
Figure 1D:

It is understood that this invention is not limited to the particular materials and methods described herein. It is also to be understood that the terminology used herein is for the purpose of describing particular embodiments and is not intended to limit the scope of the present invention, which will be limited only by the appended claims.

It must be noted that, as used in this specification and the appended claims, the singular forms "a," "an," and "the" include plural referents unless the content clearly dictates otherwise. Thus, for example, reference to "a biomarker" includes a mixture of two or more biomarkers, and the like.

The term "AUC" as used herein is an abbreviation for the area under a curve. In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area, the better, optimum is 1, a random test would have a ROC curve lying on the diagonal with an area of 0.5; for reference: J. P. Egan. Signal Detection Theory and ROC Analysis, Academic Press, New York, 1975).

The term "biological sample" refers to a sample of tissue, cells, or fluid isolated from a subject, including but not limited to, for example, blood, buffy coat, plasma, serum, blood cells (e.g., peripheral blood mononucleated cells (PBMCS), band cells, neutrophils, metamyelocytes, monocytes, or T cells), fecal matter (such as stool), urine, bone marrow, bile, spinal fluid, lymph fluid, samples of the skin, external secretions of the skin, respiratory, intestinal, and genitourinary tracts, tears, saliva, milk, organs, biopsies and also samples of in vitro cell culture constituents, including, but not limited to, conditioned media resulting from the growth of cells and tissues in culture medium, e.g., recombinant cells, and cell components.

The term "biomarker" refers to a nucleic acid molecule which is present in a sample taken from patients having human cancer as compared to a comparable sample taken from control subjects (e.g., a person with a negative diagnosis or undetectable cancer, normal or healthy subject). The biomarker can be a nucleic acid, a fragment of a nucleic acid, a polynucleotide, or an oligonucleotide that can be detected and/or quantified. Biomarkers include polynucleotides comprising nucleotide sequences from genes.

The term "CpG site" as used herein refers to stretches of DNA in a genome that are rich in GC relative to the rest of the genome. Typically, the GC content is 50% or greater in these regions, which extend over hundreds of base pairs and sometimes thousands. Often these regions mark the 5' ends of genes.

A "control amount" of a biomarker can be any amount or a range of amount which is to be compared against a test amount of a biomarker.

As used herein, the term "early detection" of cancer refers to discovering the likelihood of cancer before metastasis. Preferably, it refers to discovering the likelihood of cancer before a morphological change in a sample tissue or cell is observed.

As used herein, the terms "detect", "detecting" or "detection" may describe either the general act of discovering or discerning or the specific observation of a detectably labeled composition.

The term "gene" refers to a nucleic acid (e.g., DNA) sequence that comprises coding sequences necessary for the production of a polypeptide, precursor, or RNA (e.g., non-coding RNAs such as ribosomal RNA, transfer RNA, splicosomal RNA, microRNA). A polypeptide or non-coding RNA can be encoded by a full length coding sequence or by any portion of the coding sequence so long as the desired activity or functional properties (e.g., enzymatic activity, ligand binding, signal transduction, immunogenicity, etc.) of the full-length or fragment polypeptide are retained. Accordingly, a gene can include or exclude promoter sequences, terminators, translational regulatory sequences such as ribosome binding sites and internal ribosome entry sites, enhancers, silencers, insulators, boundary elements, replication origins, matrix attachment sites and locus control regions. The term also encompasses the coding region of a structural gene and the sequences located adjacent to the coding region on both the 5' and 3' ends for a distance of about 1 kb or more on either end such that the gene corresponds in length to the full-length mRNA. The term "gene" further includes both cDNA and genomic forms of a gene.

As used herein, the term "identity" refers to a first sequence which shares a degree of sequence identity with a second sequence, but whose sequence is not identical to that of the second sequence. For example, a polynucleotide including the wild-type sequence of a mutant gene is homologous and non-identical to the sequence of the mutant gene. In some embodiments, the degree of identity between the two sequences is sufficient to allow homologous recombination therebetween, under appropriate stringent conditions.

Techniques for determining nucleic acid and amino acid sequence identity include determining the nucleotide sequence of the mRNA for a gene and/or determining the amino acid sequence encoded thereby, and comparing these sequences to a second nucleotide or amino acid sequence.

Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100.

In some embodiments, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. See, e.g., Sambrook et al., supra; *Nucleic Acid Hybridization: A Practical Approach*, editors B. D. Hames and S. J. Higgins, (1985) Oxford; Washington, D.C.; IRL Press).

As used herein, the term "prediction" refers to the likelihood that a patient will respond either favorably or unfavorably to a drug or set of drugs, and also the extent of those responses. Thus, treatment predictive factors are variables related to the response of an individual patient to a specific treatment, independent of prognosis.

The term "methylation," as used herein, refers to the presence of a methyl group added by the action of a DNA methyl transferase enzyme to a cytosine base or bases in a region of nucleic acid, e.g., genomic DNA.

The term "methylation state," "methylation profile," or "methylation status" of a nucleic acid molecule refers to the presence or absence of one or more methylated nucleotide bases in the nucleic acid molecule. For example, a nucleic acid molecule containing a methylated cytosine is considered methylated (i.e., the methylation status of the nucleic acid molecule is methylated). A nucleic acid molecule that does not contain any methylated nucleotides is considered unmethylated.

The term "hypermethylation" refers to the average methylation status corresponding to an increased presence of methylated nucleotide bases in the nucleic acid molecule at one or a plurality of CpG dinucleotides within a DNA sequence of a test DNA sample, relative to the amount of methylated nucleotide bases in the nucleic acid molecule found at corresponding CpG dinucleotides within a normal control DNA sample.

The term "hypomethylation" refers to the average methylation status corresponding to a decreased presence of methylated nucleotide bases in the nucleic acid molecule at one or a plurality of CpG dinucleotides within a DNA sequence of a test DNA sample, relative to the amount of methylated nucleotide bases in the nucleic acid molecule found at corresponding CpG dinucleotides within a normal control DNA sample.

The term "subject" refers to humans.

The term "susceptibility" refers to a constitution or condition of the body which makes the tissues react in special ways to certain extrinsic stimuli and thus tends to make the individual more than usually susceptible to certain diseases.

The term "target site" or "target sequence" refers to a nucleic acid sequence that defines a portion of a nucleic acid to which a binding molecule will bind, provided sufficient conditions for binding exist.

The term "risk" refers to the estimated chance of getting a disease during a certain time period, such as within the next 10 years, or during the subject's lifetime.

The term "prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease.

The term "weight sum score" refers to every possible alternative being rated by a score including all objectives, individually weighted to stress the importance of different objectives.

Cancer is characterized by an abnormal growth of a cell caused by one or more mutations or modifications of a gene leading to dysregulated balance of cell proliferation and cell death. In many disease processes, such as cancer, gene promoter CpG islands acquire abnormal hypermethylation, which results in transcriptional silencing that can be inherited by daughter cells following cell division. DNA methylation causing silencing in cancer typically occurs at multiple CpG sites in the CpG islands that are present in the promoters of protein coding genes. Alterations of DNA methylation have been recognized as an important component of cancer development. DNA methylation profiling provides higher clinical sensitivity and dynamic range compared to other cancer detections. Accordingly, the present disclosure provides a method and kit for early prediction, treatment response and prognosis or recurrence monitoring of pancreatic cancer.

In some embodiments, the methylation status of one or more of the ZFP30, FBXL7, CNTN4, and KLRG2 target DNA sequences or fragments thereof in a biological sample is measured to detect pancreatic cancer or detect a predisposition to, or the incidence of, pancreatic cancer or predict treatment response, prognosis or recurrence of pancreatic cancer in a human subject.

ZFP30 gene codes for ZFP30 zinc finger protein, which is predicted to enable DNA-binding transcription factor activity, RNA polymerase II-specific and RNA polymerase II cis-regulatory region sequence-specific DNA binding activity. The ZFP30 sequence and its function are known in the art such as described on website: https://www.genecards.org/cgi-bin/carddisp.pl?gene=ZFP30.

FBXL7 gene codes for F-Box and leucine rich repeat protein 7, a member of the F-box protein family which is characterized by a 42-48 amino acid motif, the F-box, which binds to the S-phase kinase-associated protein 1 (Skp1) protein. The F-box proteins constitute one of the four subunits of E3 ubiquitin protein ligases called SCFs (SKP1-Cul1-F-box), which play a role in phosphorylation-dependent ubiquitination of proteins. The FBXL7 sequence and its function are known in the art such as described on website: https://www.genecards.org/cgi-bin/carddisp.pl?gene=FBXL7.

CNTN4 gene codes for contactin 4, a member of the contactin family of immunoglobulins. Contactins are axon-associated cell adhesion molecules that function in neuronal network formation and plasticity. The encoded protein is a glycosylphosphatidylinositol-anchored neuronal membrane protein that may play a role in the formation of axon connections in the developing nervous system. The CNTN4 sequence and its function are known in the art such as described on website: https://www.genecards.org/cgi-bin/carddisp.pl?gene=CNTN4.

KLRG2 gene codes for killer cell lectin like receptor G2, which is predicted to enable carbohydrate binding activity and to be integral component of membrane. The KLRG2 sequence and its function are known in the art such as described on website: https://www.genecards.org/cgi-bin/carddisp.pl?gene=KLRG2.

In some embodiments, the methylation includes a cytosine methylation site. In some instances, cytosine methylation comprises 5-methylcytosine (5-mCyt) and 5-hydroxymethylcytosine. In some cases, a cytosine methylation site occurs in a CpG dinucleotide motif. In other cases, a cytosine methylation site occurs in a CHG or CHH motif, in which is adenine, cytosine or thymine. In some instances, one or more CpG dinucleotide motif or CpG site forms a CpG island, a short DNA sequence rich in CpG dinucleotide. In some instances, CpG islands are typically, but not always, between about 0.2 to about 1 kb in length. In some instances, the methylation comprises CpG island methylation.

In some embodiments, the methylation status is analyzed by a methylation specific enzymatic digest; bisulfite sequencing; an analysis selected from promoter methylation, CpG island methylation, MSP, HeavyMethyl, MethyLight, and Ms-SNuPE; and other methods relying on a detection of amplified DNA. The term "MethyLight™" refers to a fluorescence-based real-time PCR technique. MethylLight is described by Eads et al., Cancer Res. 59:2302-2306, 1999, herein incorporated by reference.

The term "HeavyMethyl" assay, refers to an assay wherein methylation specific blocking probes (also referred to herein as blockers) covering CpG positions between, or covered by the amplification primers enable methylation-specific selective amplification of a nucleic acid sample.

The term "Ms-SnuPE" refers to Methylation-sensitive Single Nucleotide Primer Extension. MsSNuPE is described by Gonzalgo & Jones, Nucleic Acids Res. 25:2529-2531, 1997, herein incorporated by reference.

The term "MSP" refers to Methylation-specific PCR. MSP is described by Herman et al. Proc. Natl. Acad. Sci. USA 93:9821-9826, 1996, and by U.S. Pat. No. 5,786,146, each of which are herein incorporated by reference.

Bisulfite modification of DNA is a method to assess CpG methylation status. 5-methylcytosine is the most frequent covalent base modification in the DNA of eukaryotic cells. However, 5-methylcytosine positions cannot be identified directly by sequencing or hybridization methods, because 5-methylcytosine has the same base pairing behavior as cytosine. Moreover, the epigenetic information carried by 5-methylcytosine is completely lost during, e.g., PCR amplification. Bisulfite sequencing is a method for analyzing DNA for the presence of 5-methylcytosine is based upon the specific reaction of bisulfite with cytosine whereby, upon subsequent alkaline hydrolysis, cytosine is converted to uracil which corresponds to thymine in its base pairing behavior. However, 5-methylcytosine remains unmodified under the aforementioned conditions. Thus, the original DNA is converted in such a manner that methylcytosine, which originally could not be distinguished from cytosine by its hybridization behavior, can be detected as the only remaining cytosine using molecular biological techniques, for example, by amplification and hybridization, or by sequencing.

In one embodiment, the methylation status is detected by polymerase chain reaction, nucleic acid sequencing (such as bisulfite sequencing or pyrosequencing), bisulfite conversion, mass spectrometry, methylation specific nuclease, mass-based separation, target capture or microarray. In one embodiment, the methylation status is detected by using primers to amplify a methylated CpG of the target genes. In a further embodiment, the detection of methylation is conducted by PCR, methylation specific PCR (MSP), real-time methylation specific PCR, quantitative methylation-specific PCR (QMSP), PCR using a methylated DNA-specific binding protein or quantitative PCR.

In one embodiment of the present disclosure, primer(s) that could amplify a methylated CpG of the genes described herein might be used. The primer(s) includes at least one or more CpG dinucleotide in a region which hybridizes to the methylated CpG of the genes. Specifically, the primer(s) for amplifying a methylated CpG of the genes includes sequence(s) with about 85%, about 86%, about 87%, about 88%, about 89%, about 90%, about 91%, about 92%, about 93%, about 94%, about 95%, about 96%, about 97%, about 98%, about 99%, or about 100% identity to sequence(s) selected from the group consisting of the following sequences.

| SEQ ID No. | Primer | Sequence |
| --- | --- | --- |
| 1 | ZFP30-qMSP-F | TTT AGA GGT TTT CGC GGT CGA C |
| 2 | ZFP30-qMSP-R | AAC ACC TCG CTT TAA ACA ACT CCG |
| 3 | FBXL7-qMSP-F | GTC GGA GGT CGG TTT CGG AGT TT |
| 4 | FBXL7-qMSP-R | ATA ACT ACG ACG CAC GTC CTA CGC |
| 5 | CNTN4-qMSP-F | TTT CGG TGT TGA GGT AAG TGA GGC G |
| 6 | CNTN4-qMSP-R | TAT CCT TCG AAC AAC CCG CAC GA |
| 7 | KLRG2-qMSP-F | AAG ATT TTT TTA TTT CGC GCG TTT C |
| 8 | KLRG2-qMSP-R | AAA CGT AAC CTA ACA ACT TCG ACG AC |

Probe(s) capable of hybridizing with a methylated CpG of the genes described herein might be used. The probe(s) capable of hybridizing with a methylated CpG of the genes comprise at least one or more CpG dinucleotide in a region which hybridizes to the methylated CpG of the genes. Specifically, probe(s) might include sequence(s) with about 85%, about 86%, about 87%, about 88%, about 89%, about 90%, about 91%, about 92%, about 93%, about 94%, about 95%, about 96%, about 97%, about 98%, about 99%, or about 100% identity to sequence(s) selected from the group consisting of the following sequences.

| No. | Probe | Sequence |
|---|---|---|
| 9 | ZFP30 qMSP probe | 56-FAM/AT CGA AAA A/ZEN/C GAC TAC GTT CCT ACG/3IABkFQ (AT CGA AAA AC GAC TAC GTT CCT ACG; SEQ ID NO: 9) |
| 10 | FBXL7 qMSP probe | 56-FAM/GT AGT TAA C/ZEN/G GTT TCG TCG GGC/3IABkFQ (GT AGT TAA CG GTT TCG TCG GGC; SEQ ID NO: 10) |
| 11 | CNTN4 qMSP probe | 56-FAM/GT AGT TGT G/ZEN/C GGG TTC GGT/3IABkFQ (GT AGT TGT GC GGG TTC GGT; SEQ ID NO: 11) |
| 12 | KLRG2 qMSP probe | 56-FAM/TG GGT TTA G/ZEN/T GTA GAG GAG TTT CGT/3IABkFQ (TG GGT TTA GT GTA GAG GAG TTT CGT; SEQ ID NO: 12) |

In one embodiment, the detection of the methylation status of the target genes includes the presence of hypermethylation in the genes relative to a normal state of the target genes.

In some embodiments, the biological sample is a tissue, cell, blood, urine, serum or plasma from a patient suspected of having pancreatic cancer or a subject to be detected.

As used herein, the term "a patient suspected of having cancer" refers to an individual who has received an initial diagnosis (e.g., a CT scan showing a mass or increased biomarker level) but for whom the stage of cancer or presence or absence of methylated genes indicative of cancer is not known. The term further includes people who once had cancer (e.g., an individual in remission).

In some embodiments, a detection test to correctly predict status is measured as the sensitivity of the assay, the specificity of the assay or the area under a receiver operated characteristic (ROC) curve (AUC). The greater the area under the ROC curve, for example, the more accurate or powerful the predictive value of the test.

In one embodiment, a weighted sum score is measured to determine the methylation status in the nucleic acid sequence and genes as an indicator. The weighted sum model (WSM) is the best known and simplest multi-criteria decision analysis (MCDA)/multi-criteria decision making (MCDM) method for evaluating a number of alternatives in terms of a number of decision criteria.

In some embodiments, one or more of the biomarkers disclosed herein show a statistical difference in different samples of at least $p<0.05$. Detection tests that use these biomarkers may show an AUC of at least 0.9.

In some embodiments, the hypermethylation status of the epigenetic biomarkers in DNA sequences described herein correlates with a "poor" prognosis or the likelihood that a subject will likely respond unfavorably to a drug or set of drugs, leading to a progression of a cancer and/or to refractory of one or more therapeutic agents. In some instances, a "poor" prognosis refers to the likelihood that a subject will not respond to a drug or set of drugs, leading to a progression of a cancer. In some instances, a "poor" prognosis refers to the survival of a subject of from less than 5 years to less than 1 month. In some instances, a "poor" prognosis refers to the survival of a subject in which the survival of the subject upon treatment is from less than 5 years to less than 1 month. In some instances, a "poor" prognosis further refers to the likelihood that a subject will develop a refractory cancer toward one or more drugs.

In some embodiments, the present disclosure provides a probe having the sequence selected from the group consisting of: SEQ ID Nos: 9 to 12. In some other embodiments, the present disclosure provides a primer having the sequence selected from the group consisting of: SEQ ID Nos: 1 to 8.

In some embodiments, the present disclosure provides a kit for detecting and/or characterizing the methylation profile of the target DNA sequences described herein. In some embodiments, the target DNA sequences includes the combination selected from the group consisting of: (1) ZFP30 and FBXL7; (2) ZFP30 and CNTN4; (3) FBXL7 and CNTN4; (4) ZFP30, FBXL7, and CNTN4; and (5) ZFP30, FBXL7, CNTN4, and KLRG2.

In some instances, the kit includes a plurality of primers or probes to detect or measure the methylation status/levels of one or more target genes. Such kits include, in some instances, at least one polynucleotide that hybridizes to at least one of the methylation biomarker sequences described herein and at least one reagent for detection of gene methylation. Reagents for detection of methylation include, e.g., sodium bisulfate, polynucleotides designed to hybridize to sequence that is the product of a marker sequence if the marker sequence is not methylated (e.g., containing at least one C-U conversion), and/or a methylation-sensitive or methylation-dependent restriction enzyme. In some cases, the kits provide solid supports in the form of an assay apparatus that is adapted to use in the assay. In some instances, the kits further include detectable labels, optionally linked to a polynucleotide, e.g., a probe, in the kit. In some embodiments, the kit further includes a process unit to obtain a weighted sum score as described herein.

Optionally, one or more detectably-labeled polypeptides capable of hybridizing to the amplified portion are also included in the kit. In some embodiments, the kits include sufficient primers to amplify the target DNA sequences described herein, and optionally include detectably-labeled polynucleotides capable of hybridizing to each amplified DNA region or portion thereof. The kits further can include a methylation-dependent or methylation sensitive restriction enzyme and/or sodium bisulfite.

In some embodiments, the kits include sodium bisulfite, primers and adapters for whole target genes amplification, and polynucleotides (e.g., detectably-labeled polynucleotides) to quantify the presence of the converted methylated and or the converted unmethylated sequence of at least one cytosine from a DNA region of an epigenetic biomarker described herein.

In some embodiments, the kits include methylation sensing restriction enzymes, primers and adapters for whole target genes amplification, and polynucleotides to quantify the number of copies of at least a portion of a DNA region of an epigenetic marker described herein. In some embodiments, the kits include a methylation binding moiety and one or more polynucleotides to quantify the number of copies of at least a portion of a DNA region of a marker described herein.

The inventions described and claimed herein have many attributes and embodiments including, but not limited to, those set forth or described or referenced in this Detailed Disclosure. It is not intended to be all-inclusive and the inventions described and claimed herein are not limited to or by the features or embodiments identified in this Detailed Disclosure, which is included for purposes of illustration only and not restriction. A person having ordinary skill in the art will readily recognize that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents. Reference to any applications, patents and publications in this specification is not, and should not be taken as, an acknowledgment or any form of suggestion that they constitute valid prior art or form part of the common general knowledge in any country in the world.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants. Furthermore, titles, headings, or the like are provided to enhance the reader's comprehension of this document, and should not be read as limiting the scope of the present invention. Any examples of aspects, embodiments or components of the invention referred to herein are to be considered non-limiting.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

Without further elaboration, it is believed that one skilled in the art can utilize the present invention to its fullest extent on the basis of the preceding description. The following examples are, therefore, to be construed as merely illustrative and not a limitation of the scope of the present invention in any way.

Although the present disclosure has been described with an exemplary embodiment, various changes and modifications may be suggested to one skilled in the art. It is intended that the present disclosure encompass such changes and modifications as fall within the scope of the appended claims.

EXAMPLE

Example 1 Methylation Status of Target Nucleic Acid and Genes of in Pancreatic Cancer Tissue The β value for Illumina Methylation 450K array-based data was generated from The Cancer Genome Atlas (TCGA) Research Network. The target nucleic acid and genes shown in Table 1 were selected when the Δβ value (the value of tumor tissues subtracts that of normal tissues) is higher than 0.3.

TABLE 1

| Avg | Patients with Pancreatic Cancer | | | Healthy |
|---|---|---|---|---|
| | β value (Tumor) | β value (Normal) | β value (Plasma) | β value (Plasma) |
| ZFP30 | 0.4325 | 0.048 | 0.3102 | 0.1774 |
| KLRG2 | 0.5729 | 0.2390 | 0.2766 | 0.1553 |
| FBXL7 | 0.4277 | 0.0995 | 0.3221 | 0.1526 |
| CNTN4 | 0.4514 | 0.0985 | 0.2706 | 0.0959 |

FIGS. 1A-1D show the difference of methylation status (β value) of target nucleic acid and genes between tumor tissues and adjacent normal tissues (n=185). Darker color indicates tissues with higher methylation status according to Illumina Methylation 450K array-based data.

Figure 2A:
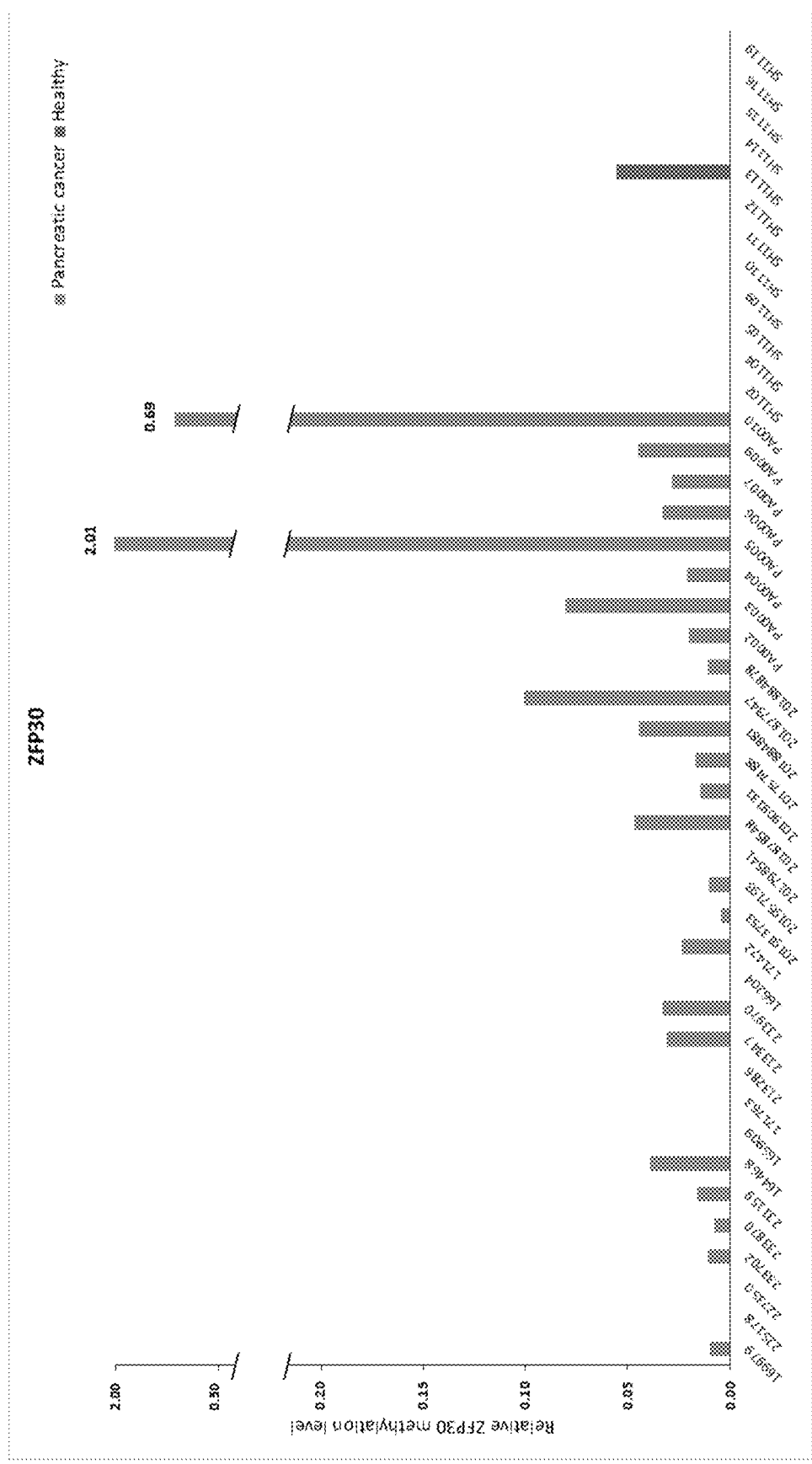
FIG. 2A shows differences in early detection of methylation status of target gene ZFP30 in plasma samples of pancreatic cancer patients (n=31) and healthy subjects (n=12).
Figure 2B:
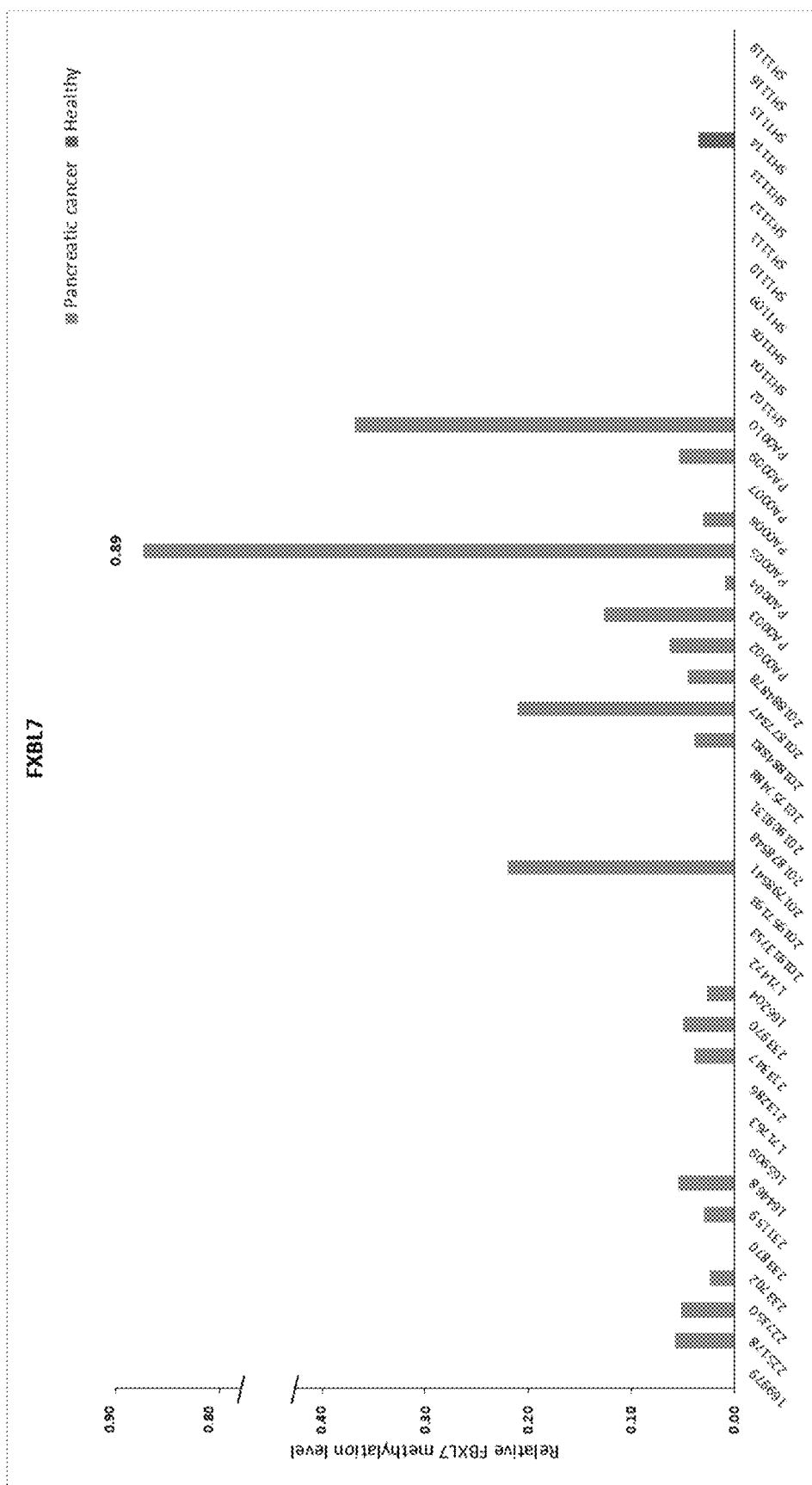
FIG. 2B shows differences in early detection of methylation status of target gene FBXL7 in plasma samples of pancreatic cancer patients (n=31) and healthy subjects (n=12).
Figure 3:
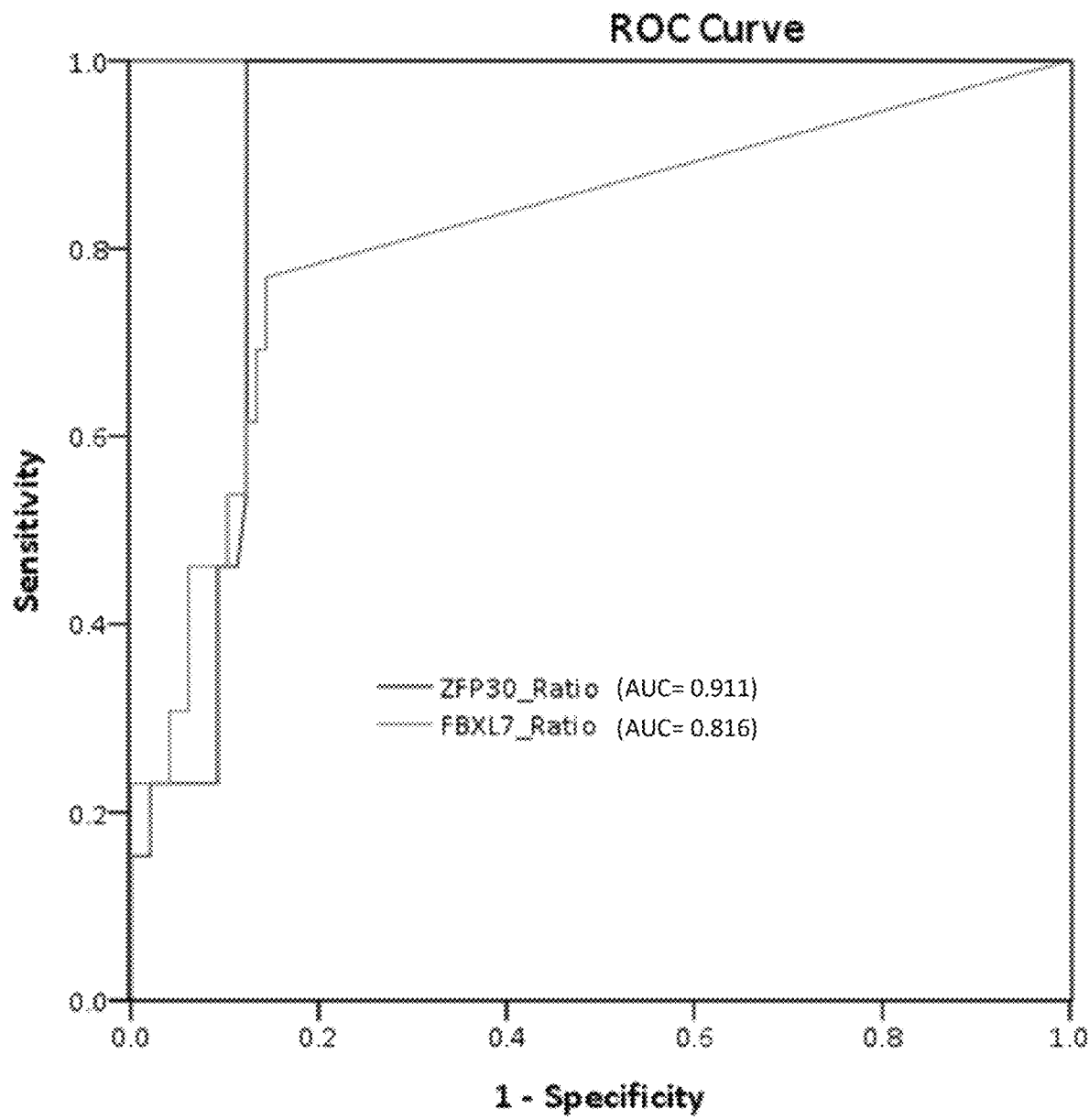
FIG. 3 shows ROC Curve Analysis based on the early detection of the methylation status of target genes in pancreatic cancer patients and healthy subjects.

Example 2 Early Detection of Methylation Status of Target Genes in Plasma Samples of Pancreatic Cancer Patient and Healthy Subjects The cfDNA extracted from plasma of pancreatic cancer patients and healthy subjects were analyzed by Probe-based methylation specific real-time PCR (qMSP). The representative figures FIGS. 2A and 2B show the methylation status of target genes ZFP30 (FIG. 2A) and FBXL7 (FIG. 2B) in plasma samples of pancreatic cancer patients (n=31) and healthy subjects (n=12), revealing the distinctions between the two groups. Pancreatic cancer patients exhibit higher methylation levels in both target genes compared to healthy subjects.

Example 3 Performance of the Early Detection of Methylation Status of Target Genes in Plasma Samples of Pancreatic Cancer Patients and Healthy Subjects Combining the methylation status results of target genes ZFP30 and FBXL7 in plasma samples of the two groups, the following tables illustrates the sensitivity, specificity, and accuracy of the early detection of methylation status of the two target genes in Taiwanese cohort and translational cohort. The sensitivity, specificity, and accuracy are 100.0%, 87.6%, 89.1% respectively in Taiwanese cohort; 87.5%, 87.6%, 87.6% respectively in Taiwanese cohort-American cohort.

TABLE 2

The sensitivity, specificity, and accuracy of the early detection of methylation status of target genes ZFP30 and FBXL7 in Taiwanese cohort (N = 110).

| | | Pancreatic Cancer | Healthy Individual | Measures |
|---|---|---|---|---|
| Taiwan + USA N = 110 | Positive Detection | True positive (TP) 13 | False positive (FP) 12 | Positive predictive value (PPV) 52.0% |
| | Negative Detection | False negative (FN) 0 | True negative (TN) 85 | Negative predictive value (NPV) 100.0% |
| | Measures | Sensitivity 100.0% | Specificity 87.6% | Accuracy 89.1% |

TABLE 3

The sensitivity, specificity, and accuracy of the early detection of methylation status of target genes ZFP30 and FBXL7 in Taiwanese-American cohort (N = 121).

| | | Pancreatic Cancer | Healthy Individual | Measures |
|---|---|---|---|---|
| Taiwan + USA N = 121 | Positive Detection | True positive (TP) 21 | False positive (FP) 12 | Positive predictive value (PPV) 63.6% |
| | Negative Detection | False negative (FN) 3 | True negative (TN) 85 | Negative predictive value (NPV) 96.6% |
| | Measures | Sensitivity 87.5% | Specificity 87.6% | Accuracy 87.6% |

Example 4 Receiver Operating Characteristic Curve Analysis of the Early Detection of Methylation Status of Target Genes in Plasma Samples of Pancreatic Cancer Patients and Healthy Subjects Based on the early detection results of target genes ZFP30 and FBXL7 in plasma samples of the two groups, the Receiver Operating Characteristic (ROC) Curve were constructed for the two target genes ZFP30 and FBXL7, including both individual and combined analyses. The analysis results indicate that the optimal diagnostic model is achieved when using ZFP30 gene with an Area Under the Curve (AUC) value of 0.911; while using FBXL7 gene gives an Area Under the Curve (AUC) value of 0.816.

What is claimed is:

1. A method for determining an increased risk of pancreatic cancer in a human subject, wherein the method comprises:
   (a) extracting (i) cell-free DNA (cfDNA) from a biological sample of the human subject or (ii) genomic DNA from a biological sample from a pancreatic tumor tissue of the human subject, wherein the cfDNA or the genomic DNA comprises the target of ZFP30 DNA;
   (b) assaying methylation level of one or more CpG sites of the ZFP30 from the cfDNA or the genomic DNA using methylation-specific polymerase chain reaction (MSP) assay, wherein a pair of ZFP30 methylation-specific primers used in the assay comprises SEQ ID NO: 1 and SEQ ID NO: 2;
   (c) comparing the methylation level of step (b) to the methylation level from a control sample without pancreatic cancer; and
   (d) determining an increased risk of pancreatic cancer in the human subject based upon a higher methylation level detected in the sample as compared to the control sample.

2. The method of claim 1, wherein the method further comprises measuring the methylation level of one or more CpG sites in FBXL7 using a pair of primers specific to FBXL7 or a fragment thereof comprising: extracting genomic DNA from a biological sample of a subject suspected of having or having a pancreatic cancer; treating the resulting extract with bisulfate; amplifying the bisulfite-treated genomic DNA with primers consisting of a pair of primers specific for FBXL7; and measuring the methylation level of one or more CpG sites in FBXL7 by a polymerase chain reaction (PCR).

3. The method of claim 2, wherein the pair of primers specific for FBXL7 used to amplify the bisulfite-treated genomic DNA have has a sequence identity of at least about 85% to sequences of SEQ ID NOs: 3 and 4.

4. The method of claim 2, wherein an FBXL7 methylation-specific probe is further used to measure the methylation level of one or more CpG sites in FBXL7 or the fragment thereof.

5. The method of claim 4, wherein the FBXL7 methylation-specific probe comprises a sequence with at least 85% identity to SEQ ID No: 10.

6. The method of claim 2, wherein the method further comprises measuring the methylation level of one or more CpG sites in CNTN4 and/or KLRG2 using a pair of primers specific to CNTN4 and/or KLRG2, or a fragment thereof comprising: extracting genomic DNA from a biological sample of a subject suspected of having or having pancreatic cancer; treating the resulting extract with bisulfate; amplifying the bisulfite-treated genomic DNA with primers consisting of a pair of primers specific for CNTN4 or a fragment thereof and/or primers consisting of a pair of primers specific for KLRG2 or a fragment thereof; and measuring the methylation level of one or more CpG sites in CNTN4 and/or KLRG2 or a fragment thereof by a polymerase chain reaction (PCR).

7. The method of claim 6, wherein the pair of primers specific for CNTN4 used to amplify the bisulfite-treated genomic DNA has a sequence identity of at least about 85% to sequences of SEQ ID NOs: 5 and 6; and the pair of primers specific for KLRG2 used to amplify the bisulfite-treated genomic DNA has a sequence identity of at least about 85% to sequences of SEQ ID NOs: 7 and 8.

8. The method of claim 6, wherein a CNTN4 methylation-specific probe, a KLRG2 methylation-specific probe, or a combination thereof is further used to measure the methylation level of one or more CpG sites in CNTN4 and KLRG2 or the fragments thereof.

9. The method of claim 8, wherein the CNTN4 methylation-specific probe comprises a sequence with at least 85% identity to SEQ ID No: 11 and the KLRG2 methylation-specific probe has a sequence with at least 85% identity to SEQ ID No: 12.

10. A method for determining an increased risk of pancreatic cancer in a human subject, wherein the method comprises:
   (a) providing (i) a biological sample containing DNA from the human subject and extracting cell-free DNA (cfDNA) from the biological sample or (ii) a biological sample from a pancreatic tumor tissue of the human subject and extracting genomic DNA from the biological sample, wherein the cfDNA or the genomic DNA comprises a target of ZFP30 DNA;
   (b) assaying methylation level of a CpG site of the ZFP30 from the cfDNA or the genomic DNA using methylation-specific polymerase chain reaction (MSP) assay, wherein a ZFP30 methylation-specific probe used in the assay comprises SEQ ID NO: 9;
   (c) comparing the methylation level of step (b) to the methylation level from a control sample without pancreatic cancer; and
   (d) determining an increased risk of pancreatic cancer in the human subject based upon a higher methylation level detected in the sample as compared to the control sample.

11. The method of claim 10, wherein a pair of primers specific for ZFP30 is further used in the assay, and the pair of primers comprises SEQ ID NO: 1 and SEQ ID NO: 2.

12. The method of claim 10, wherein the cfDNA or the genomic DNA further comprises a target of FBXL7 DNA, and wherein the method further comprises assaying a methylation level of one or more CpG sites in the FBXL7 from the cfDNA or the genomic DNA using MSP assay.

13. The method of claim 12, wherein a pair of primers specific for FBXL7 is used in the assay, wherein the pair of primers specific for FBXL7 comprises SEQ ID NO: 3 and SEQ ID NO: 4.

14. The method of claim 12, wherein an FBXL7 methylation-specific probe is used in the assay.

15. The method of claim 14, wherein the FBXL7 methylation-specific probe comprises SEQ ID NO: 10.

16. The method of claim 12, wherein the cfDNA or the genomic DNA further comprises a target of CNTN4 DNA and/or a target of KLRG2 DNA, and wherein the method further comprises assaying methylation levels of one or more CpG sites in the CNTN4 and/or the KLRG2 from the cfDNA or the genomic DNA using MSP assay.

17. The method of claim 16, wherein a pair of primers specific for CNTN4 and/or a pair of primers specific for KLRG2 is used in the assay, and the pair of primers CNTN4 comprises SEQ ID NO: 5 and SEQ ID NO: 6, and the pair of primers specific for KLRG2 comprises SEQ ID NO: 7 and SEQ ID NO: 8.

18. The method of claim 16, wherein an CNTN4 methylation-specific probe, an KLRG2 methylation-specific probe, or a combination thereof is used in the assay.

19. The method of claim 18, wherein the CNTN4 methylation-specific probe comprises SEQ ID NO: 11, and the KLRG2 methylation-specific probe comprises SEQ ID NO: 12.

20. The method of claim 10, wherein the biological sample is a tissue sample, a pancreatic juice sample, a pancreatic cyst fluid sample, a stool sample, a cell sample, a blood sample, a urine sample, a serum sample, or a plasma sample.

21. A method for determining an increased risk of pancreatic cancer in a human subject, wherein the method comprises:
(a) providing (i) a biological sample containing DNA from the human subject and extracting cell-free DNA (cfDNA) from the biological sample or (ii) a biological sample from a pancreatic tumor tissue of the human subject and extracting genomic DNA from the biological sample, wherein the cfDNA or the genomic DNA comprises a target of ZFP30 DNA and a target of FBXL7 DNA;
(b) assaying methylation levels of a CpG site of the ZFP30 and the FBXL7 from the cfDNA or the genomic DNA using methylation-specific polymerase chain reaction (MSP) assay, wherein a pair of primers for ZFP30 used in the assay comprises SEQ ID NO: 1 and SEQ ID NO: 2, and a pair of primers for FBXL7 used in the assay comprise SEQ ID NO: 3 and SEQ ID NO: 4;
(c) comparing the methylation level of step (b) to the methylation level from a control sample without pancreatic cancer; and
(d) determining an increased risk of pancreatic cancer in the human subject based upon a higher methylation level detected in the sample as compared to the control sample.

22. The method of claim 21, wherein the cfDNA or the genomic DNA further comprises a target of CNTN4 DNA and/or a target of KLRG2 DNA, and wherein the method further comprises assaying methylation levels of one or more CpG sites in the CNTN4 and/or the KLRG2 from the cfDNA or the genomic DNA using MSP assay; and wherein a pair of primers specific for CNTN4 and/or a pair of primers specific for KLRG2 is used in the assay, and the pair of primers CNTN4 comprises SEQ ID NO: 5 and SEQ ID NO: 6, and the pair of primers specific for KLRG2 comprises SEQ ID NO: 7 and SEQ ID NO: 8.

23. The method of claim 22, wherein a ZFP30 methylation-specific probe, a FBXL7 methylation-specific probe, a CNTN4 methylation-specific probe, a KLRG2 methylation-specific probe, or a combination thereof is further used in the assay, wherein the ZFP30 methylation-specific probe comprises SEQ ID NO: 9, the FBXL7 methylation-specific probe comprises SEQ ID NO: 10, the CNTN4 methylation-specific probe comprises SEQ ID NO: 11, and the KLRG2 methylation-specific probe comprises SEQ ID NO: 12.

* * * * *

SEQUENCE LISTING

```
Sequence total quantity: 12
SEQ ID NO: 1           moltype = DNA   length = 22
FEATURE                Location/Qualifiers
source                 1..22
                       mol_type = other DNA
                       organism = synthetic construct
```

```
SEQUENCE: 1
tttagaggtt ttcgcggtcg ac                                                    22

SEQ ID NO: 2           moltype = DNA    length = 24
FEATURE                Location/Qualifiers
source                 1..24
                       mol_type = other DNA
                       organism = synthetic construct
SEQUENCE: 2
aacacctcgc tttaaacaac tccg                                                  24

SEQ ID NO: 3           moltype = DNA    length = 23
FEATURE                Location/Qualifiers
source                 1..23
                       mol_type = other DNA
                       organism = synthetic construct
SEQUENCE: 3
gtcggaggtc ggtttcggag ttt                                                   23

SEQ ID NO: 4           moltype = DNA    length = 24
FEATURE                Location/Qualifiers
source                 1..24
                       mol_type = other DNA
                       organism = synthetic construct
SEQUENCE: 4
ataactacga cgcacgtcct acgc                                                  24

SEQ ID NO: 5           moltype = DNA    length = 25
FEATURE                Location/Qualifiers
source                 1..25
                       mol_type = other DNA
                       organism = synthetic construct
SEQUENCE: 5
tttcggtgtt gaggtaagtg aggcg                                                 25

SEQ ID NO: 6           moltype = DNA    length = 23
FEATURE                Location/Qualifiers
source                 1..23
                       mol_type = other DNA
                       organism = synthetic construct
SEQUENCE: 6
tatccttcga acaacccgca cga                                                   23

SEQ ID NO: 7           moltype = DNA    length = 25
FEATURE                Location/Qualifiers
source                 1..25
                       mol_type = other DNA
                       organism = synthetic construct
SEQUENCE: 7
aagatttttt tatttcgcgc gtttc                                                 25

SEQ ID NO: 8           moltype = DNA    length = 26
FEATURE                Location/Qualifiers
source                 1..26
                       mol_type = other DNA
                       organism = synthetic construct
SEQUENCE: 8
aaacgtaacc taacaacttc gacgac                                                26

SEQ ID NO: 9           moltype = DNA    length = 25
FEATURE                Location/Qualifiers
source                 1..25
                       mol_type = other DNA
                       organism = synthetic construct
SEQUENCE: 9
atcgaaaaac gactacgttc ctacg                                                 25

SEQ ID NO: 10          moltype = DNA    length = 22
FEATURE                Location/Qualifiers
source                 1..22
                       mol_type = other DNA
                       organism = synthetic construct
SEQUENCE: 10
gtagttaacg gtttcgtcgg gc                                                    22

SEQ ID NO: 11          moltype = DNA    length = 19
FEATURE                Location/Qualifiers
source                 1..19
                       mol_type = other DNA
```

-continued

```
                       organism = synthetic construct
SEQUENCE: 11
gtagttgtgc gggttcggt                                          19

SEQ ID NO: 12          moltype = DNA  length = 25
FEATURE                Location/Qualifiers
source                 1..25
                       mol_type = other DNA
                       organism = synthetic construct
SEQUENCE: 12
tgggtttagt gtagaggagt ttcgt                                   25
```